United States Patent
Ivory et al.

(10) Patent No.: US 8,303,789 B1
(45) Date of Patent: Nov. 6, 2012

(54) CONTROL OF ELECTROLYTE SOLUTION IN NANOFLUIDIC CHANNELS

(75) Inventors: Cornelius F. Ivory, Pullman, WA (US); Sang M. Han, Albuquerque, NM (US); Youn-Jin Oh, San Ramon, CA (US)

(73) Assignee: STC.UNM, Albuquerque, NM (US)

( * ) Notice: Subject to any disclaimer, the term of this patent is extended or adjusted under 35 U.S.C. 154(b) by 252 days.

(21) Appl. No.: 12/721,860

(22) Filed: Mar. 11, 2010

Related U.S. Application Data

(63) Continuation-in-part of application No. PCT/US2009/061314, filed on Oct. 20, 2009.

(60) Provisional application No. 61/106,648, filed on Oct. 20, 2008.

(51) Int. Cl.
*G01N 27/414* (2006.01)
*G01N 27/447* (2006.01)

(52) U.S. Cl. ........ 204/450; 204/454; 204/548; 204/600; 204/644

(58) Field of Classification Search ............ 204/450, 204/451, 454, 548, 600, 601, 644
See application file for complete search history.

(56) References Cited

U.S. PATENT DOCUMENTS

| 8,105,471 | B1 * | 1/2012 | Han et al. ............. 204/451 |
| 2003/0127329 | A1 | 7/2003 | DeVoe et al. |
| 2006/0054504 | A1 | 3/2006 | Lee et al. |
| 2006/0169587 | A1 | 8/2006 | Lopez et al. |
| 2008/0251382 | A1 | 10/2008 | Han et al. |

OTHER PUBLICATIONS

Karnik et al, Applied Physics Letters 2006, 88, 123114.*
Oh et al, Lab on a Chip 2009, 9, pp. 1609-1617.*
International Searching Authority, International Search Report, International Application No. PCT/US2009/061314, May 12, 2010, 1 Pages.

* cited by examiner

*Primary Examiner* — Kaj K Olsen
(74) *Attorney, Agent, or Firm* — MH2 Technology Law Group LLP

(57) ABSTRACT

Various embodiments provide an exemplary lab-on-a-chip (LOC) system that serves as an analytical tool and/or as a separation medium for an electrolyte solution including various charged molecular species. The LOC system can include an integrated nanofluidic FET device in combination with suitable analysis systems. By applying and controlling a longitudinal electric field and a transverse electric potential, the flow and the pH of the electrolyte solution in the nanofluidic channels can be controlled.

19 Claims, 9 Drawing Sheets

200

220

CONTROL OF ELECTROLYTE SOLUTION IN NANOFLUIDIC CHANNELS

RELATED APPLICATIONS

This application is a continuation-in-part of PCT/US09/61314, entitled "High Resolution Focusing and Separation of Proteins in Nanofluidic Channels," filed Oct. 20, 2009, the complete disclosure of which is incorporated herein by reference, which claims priority from U.S. Provisional Patent Application Ser. No. 61/106,648, filed Oct. 20, 2008, which is hereby incorporated by reference in its entirety.

GOVERNMENT RIGHTS

This invention was made with Government support under Contract No. CTS-0404124 awarded by the National Science Foundation. The U.S. Government has certain rights in this invention.

FIELD OF THE INVENTION

This invention relates generally to electrolyte solutions in nanofluidic channels and, more particularly, to systems and methods for controlling a flow and pH of the electrolyte solutions in nanofluidic channels.

BACKGROUND OF THE INVENTION

In order to characterize and understand protein function and regulation, proteins must be first separated and then detected. The most common technique for protein separations is gel electrophoresis. Today, 1-D and 2-D polyacrylamide gel electrophoresis (PAGE) setup is commercially available and widely used as a standard technique. Despite its widespread use, however, the PAGE technique has its own limitations, such as requiring a large amount of sample, low reproducibility, breakdown under high electric field, and low dynamic range.

To overcome these limitations of the conventional PAGE technique, a number of new separation platforms have emerged using microfluidic and nanofluidic channels. For example, micro/nanofluidic devices fabricated using conventional semiconductor manufacturing methods potentially use smaller sample amounts, lower electrical field, shorter analysis time, and higher throughput than the PAGE technique. It is desirable to provide an analytical tool and separation medium to control bio-separation, detection, and chemical analysis using nanofluidic devices. Specifically, there is a need to overcome these and other problems of the prior art and to provide systems and methods for controlling a flow and/or a pH value of an electrolyte solution that contains charged species in nanofluidic devices.

SUMMARY OF THE INVENTION

According to various embodiments, the present teachings include a method for controlling an electrolyte solution in a nanofluidic channel. Specifically, a plurality of nanofluidic channels in a substrate can be provided with each nanofluidic channel including an insulating surface layer, such that an electrolyte solution in the nanofluidic channel can be insulated from the substrate. A multi-gate nanofluidic field-effect-transistor (FET) can be configured to have a plurality of gates in the substrate. The plurality of gates can be spaced along a length direction of the nanofluidic channels with each gate surrounding the nanofluidic channel perpendicularly to the length direction of the nanofluidic channels. In this method, an electric potential $V_{EO}$ can be applied to a length of the electrolyte solution in the nanofluidic channels to generate an electroosmotic (EO) flow of the electrolyte solution along the nanofluidic channels. The electrolyte solution can include a plurality of charged species. A gate electric potential $V_G$ can then be applied to each FET gate to generate a leakage current to change at least one of a direction and a speed of the EO flow and a pH value of the electrolyte solution.

According to various embodiments, the present teachings also include a lab-on-a-chip system. The lab-on-a-chip system can include a nanofluidic array disposed in a substrate. The nanofluidic array can include a plurality of nanofluidic channels with each nanofluidic channel including an insulating surface layer such that an electrolyte solution in the nanofluidic channel can be insulated from the substrate. A power supply can be included for applying an electric potential to a length of the protein mixture solution to form a longitudinal electric field along each nanofluidic channel. A multi-gate nanofluidic field-effect-transistor (FET) can also be included having a plurality of gates in the substrate. The plurality of gates can be spaced along a length direction of the nanofluidic channels with each gate in the substrate surrounding the nanofluidic channel. The lab-on-a-chip system can further include an IR spectroscopy system configured such that the nanochannel array can be disposed along the direction of IR propagation from an IR source of the IR spectroscopy system.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to exemplary embodiments of the invention, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

Exemplary embodiments provide systems and methods for focusing and/or separating proteins using nanofluidic channels and/or arrays of nanofluidic channels. The disclosed nanofluidic apparatus, systems and methods can provide a versatile platform to separate proteins, for example low-abundance proteins, with high resolution, using separation techniques including for example, isoelectric focusing (IEF), dynamic field gradient focusing (DFGF) and/or a combination thereof. In embodiments, a control scheme using multi-gate nanofluidic field-effect-transistors (FETs) can be combined with the disclosed nanofluidic technique.

In embodiments, a stable pH gradient can be established in nanofluidic channels without the use of ampholytes upon an application of a longitudinal electric field to the protein mixture solution in the nanofluidic channels, thereby allowing for isoelectric focusing (IEF). In embodiments, the balance between electroosmosis and electrophoresis (e.g., electrophoretic mobility vs. counter flow buffer) can also be controlled dynamically in nanofluidic channels to achieve dynamic field gradient focusing (DFGF). In embodiments, IEF and DFGF can work simultaneously in the same system to concentrate, focus and/or separate proteins.

Various embodiments therefore allow high resolution IEF and/or DFGF and separation of proteins using the nanochannel array, in combination with electroosmosis, electrophoresis, pH gradient, protein-wall interactions, and different mobility of proteins. As compared with conventional techniques, the disclosed systems and methods do not use ampholytes to build up the pH gradient, do not use multi buffer ionic species to induce diffusion potential, and do not use surface treatment to enhance isoelectric focusing. The disclosed systems and methods, however, can use low electric potential to achieve isoelectric focusing of proteins. The low electric potential for IEF can be, for example, about 5 V or less or in embodiments, about 3 V or less.

Figure 1:
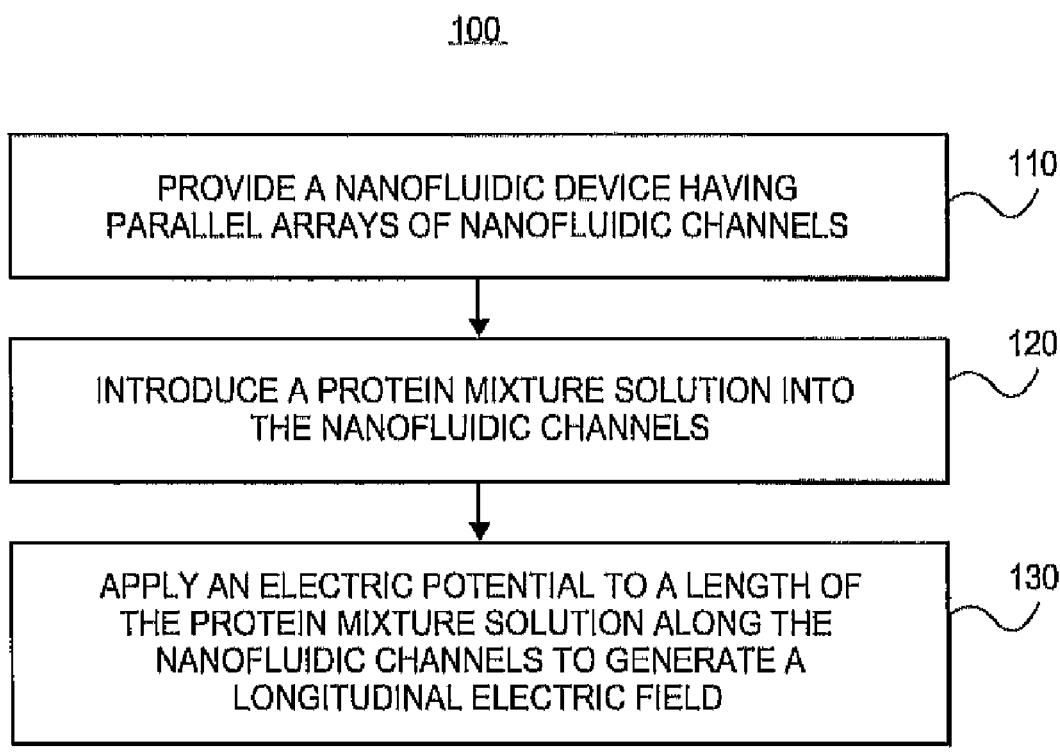
FIG. 1 depicts an exemplary method for focusing and/or separating proteins in accordance with various embodiments of the present teachings.

FIG. 1 depicts an exemplary method 100 for focusing and/or separating proteins in accordance with various embodiments of the present teachings. FIGS. 2A-2E depict a schematic of the exemplary nanofluidic device and system to conduct high-resolution focusing and separation of proteins within nanochannels in accordance with various embodiments of the present teachings.

Figure 2A:
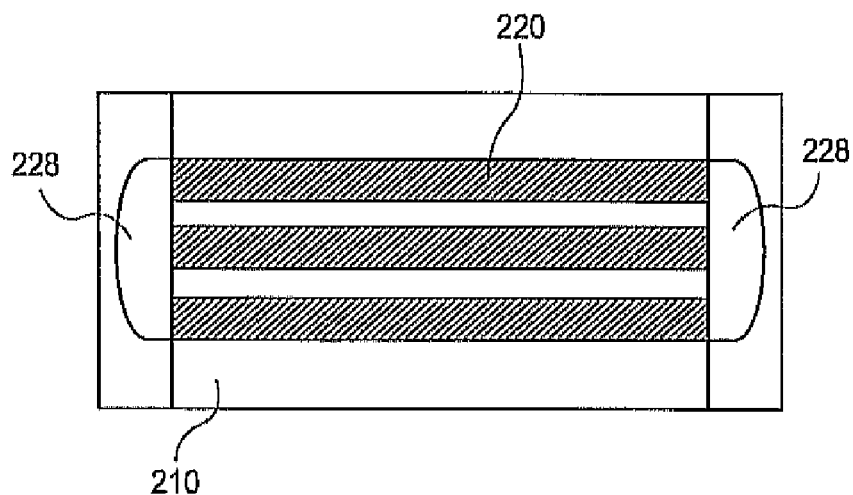
FIGS. 2A-2B depict portions of an exemplary nanofluidic device in accordance with various embodiments of the present teachings.
Figure 2B:
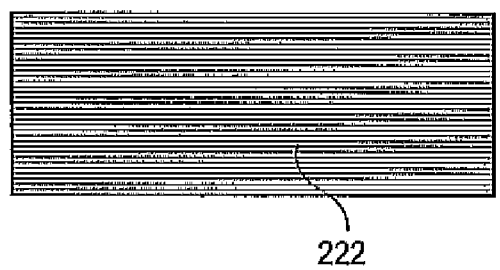
Figure 2C:
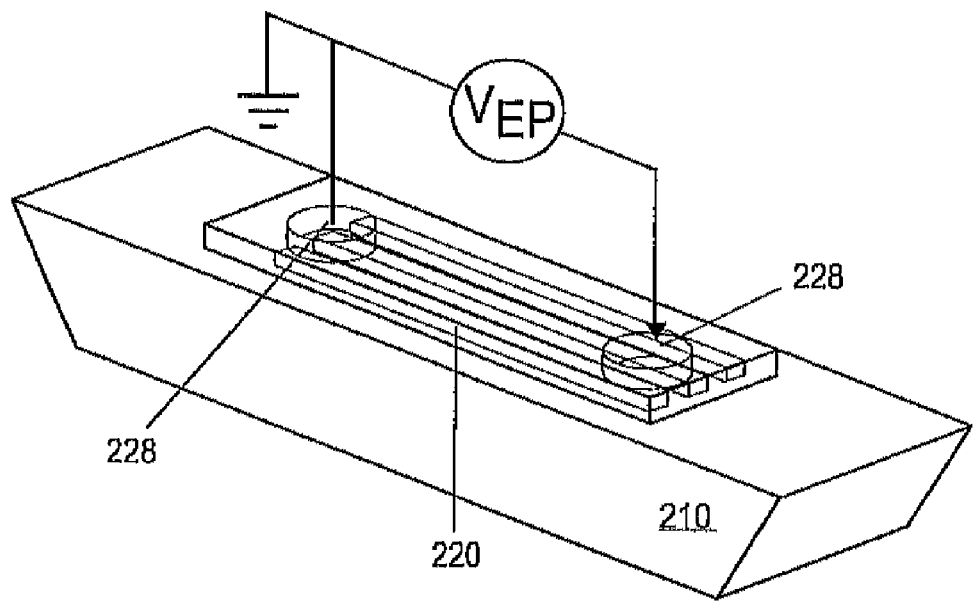
FIG. 2C depicts an exemplary nanofluidic system in accordance with various embodiments of the present teachings.
Figure 2D:
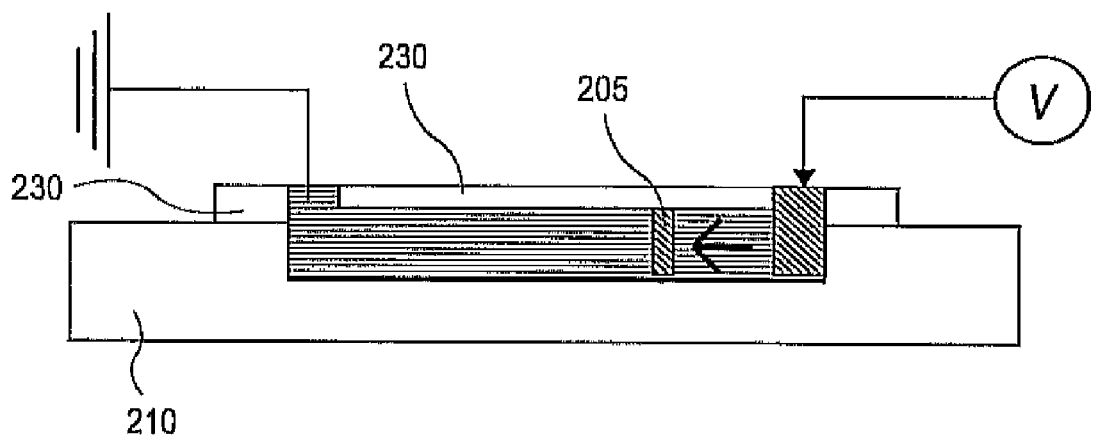
FIG. 2D depicts an exemplary nanofluidic channel during protein focusing in accordance with various embodiments of the present teachings.
Figure 2E:
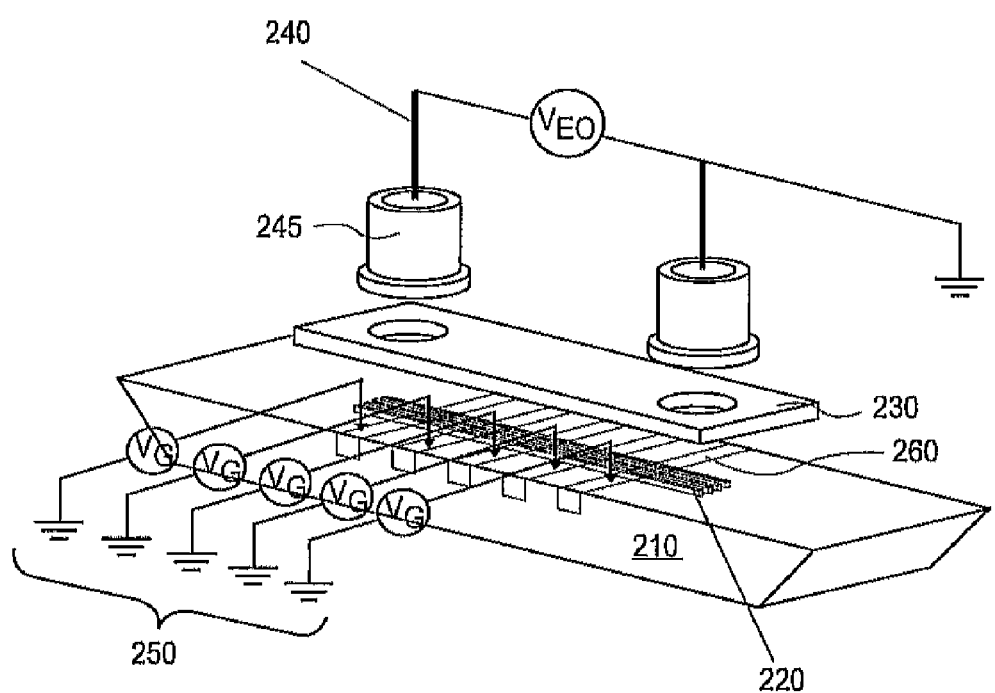
FIG. 2E depicts another exemplary nanofluidic system in accordance with various embodiments of the present teachings.

Specifically, FIG. 2A depicts a schematic top view of a portion of an exemplary nanofluidic device 200; FIG. 2B depicts a close-up schematic of an exemplary nanofluidic array 220 of the device 200; FIG. 2C depicts an exemplary system 220C for focusing and/or separating proteins using the device 200; FIG. 2D depicts a cross-sectional schematic of an exemplary nanochannel when used to focus/separate proteins; and FIG. 2E depicts another exemplary system 200E using a control scheme of multi-gate nanofluidic FETs (field-effect-transistors) in accordance with various embodiments of the present teachings.

Note that although the method 100 will be described in reference to FIGS. 2A-2E for illustrative purposes, the process of method 100 is not limited to the structures shown in FIGS. 2A-2E. In addition, while the method 100 of FIG. 1 is illustrated and described below as a series of acts or events, it will be appreciated that the present teachings are not limited by the illustrated ordering of such acts or events. For example, some acts may occur in different orders and/or concurrently with other acts or events apart from those illustrated and/or described herein. Also, not all illustrated steps may be required to implement a methodology in accordance with one or more aspects or embodiments of the present invention. Further, one or more of the acts depicted herein may be carried out in one or more separate acts and/or phases.

At 110 of FIG. 1, a nanofluidic device 200 can be provided as shown in FIGS. 2A-2E. The device 200 can include one or more nanochannel arrays 220 formed in a substrate 210 (see FIGS. 2C-2E). In embodiments, the one or more nanochannel arrays 220 can be configured to be parallel. The substrate 210 can be made of any suitable substrate material including for example silicon, a III-V substrate, ceramic, glass, plastic, etc. In embodiments, the substrate material can be a semiconducting material including silicon and/or germanium.

Each array 220 can include a plurality of nanochannels 222 (or nanofluidic channels). In embodiments, each array 220 can have a desired number of nanofluidic channels 222, for example, about 2 to about $10^8$. In embodiments, the nanofluidic channels 222 can be configured to be substantially parallel. In certain embodiments, each array 220 can include from about 120 to about 180 parallel nanochannels, although other number of parallel channels can also be used for the disclosed nanofluidic device.

In embodiments, the nanochannel 222 can have at least one minor dimension, for example, depth of about 1000 nanometers or less, in embodiments, of about 500 nanometers or less. In an exemplary embodiment, the nanochannel 222 can have at least one minor dimension, for example, width of about 1000 nanometers or less, in embodiments, ranging from about 15 nanometers to about 100 nanometers. In embodiments, the nanochannel 222 can have one of the width and the depth of about 1000 nm or less. In embodiments, the nanochannel 222 can have a length of at least about 100 micrometers, for example, ranging from about 100 micrometers to about 2 centimeters or to about 10 centimeters.

The nanochannels 222 and their arrays 220 can be fabricated using suitable semiconductor fabrication processes. For example, the nanochannels 222 can be formed in the substrate 210 by a lithography process, such as interferometric lithography (IL) and an etching process, such as a plasma etching process of the substrate 210. In embodiments, an electrically insulating layer (see 325 of FIG. 3B) can be formed on substrate wall surfaces of each nanochannel 222. The insulating layer can be formed of, for example, $SiO_2$, $Si_3N_4$, $Al_2O_3$, $TiO_2$, and/or a combination thereof. In an exemplary embodiment, a thermally grown $SiO_2$ layer having a thickness of, for example, about 100 nm or less, can be used as an electrically insulating layer between the substrate nanochannel walls and the fluid flowing through each channel.

In embodiments, the device 200 can include a plurality of end wells 228. The end wells 228 can be connected with each nanochannel 222 and/or nanochannel array 220, wherein, for example, liquid can pass through the nanochannels 222 from the end well 228 by capillary force. In embodiments, the end wells 228 can be used as liquid or solution reservoirs for introducing and storing the liquid or solution.

In embodiments, as shown in FIGS. 2D-2E, the nanochannels 222 of the nanofluidic device 200 can be sealed with an optically transparent material 230, for example, a Pyrex cover, which can be bonded onto the substrate 210, for example, by anodic bonding to form the nanofluidic device 200. In embodiments, the optically transparent material 230 can also include, for example, glass, quartz, polydimethylsiloxane (PDMS), and/or plastic.

In various exemplary embodiments, the nanochannel 222 can have a width on the order of a thickness of electric double layer (EDL). Due to this dimensional comparability, the EDLs can overlap in nanofluidic channels, giving rise to unique characteristics that are not readily achievable in conventional microfluidic channels, but can be exploited for biomolecular separations. There can be many advantages provided by nanofluidic channels. For example, electroosmosis (EO) can be a dominant mechanism of molecular transport over electrophoresis (EP) and can be controlled by modulating the $\zeta$-potential with an externally applied electric potential (V) to the nanochannel walls. In another example, electrostatic interaction of charged biomolecules and nanochannel walls can be more pronounced than in microfluidic channels and can allow one to control the electrokinetic mobility of charged molecules much more effectively than in microchannels. Additionally, differently sized molecules, such as DNA and protein molecules, can be separated using the nanoscale sieving structure, where surface charges can be controlled.

At 120 of FIG. 1, a protein-containing solution or a protein mixture solution can be introduced into the nanofluidic channels 222 and/or their arrays 220. For example, the protein mixture solution can be introduced into one of the end wells 228 and can further fill the nanofluidic channels 222 and/or their arrays 220 by capillary force or by electroosmosis.

In embodiments, prior to introducing the protein mixture solution, both the end wells 228 and/or the nanochannels 222/arrays 220 can first be filled with a buffer solution, for example, by capillary force. In embodiments, the buffer solution can be selected according to the specification of particular proteins and can be used to dilute proteins. For example, the buffer solution can have a pH ranging from about 2 to about 10 and an ionic strength ranging from about 0.1 mM to about 100 mM. Depending on the proteins used, other pH ranges and ionic strengths can also be included in various embodiments.

Figure 3A:
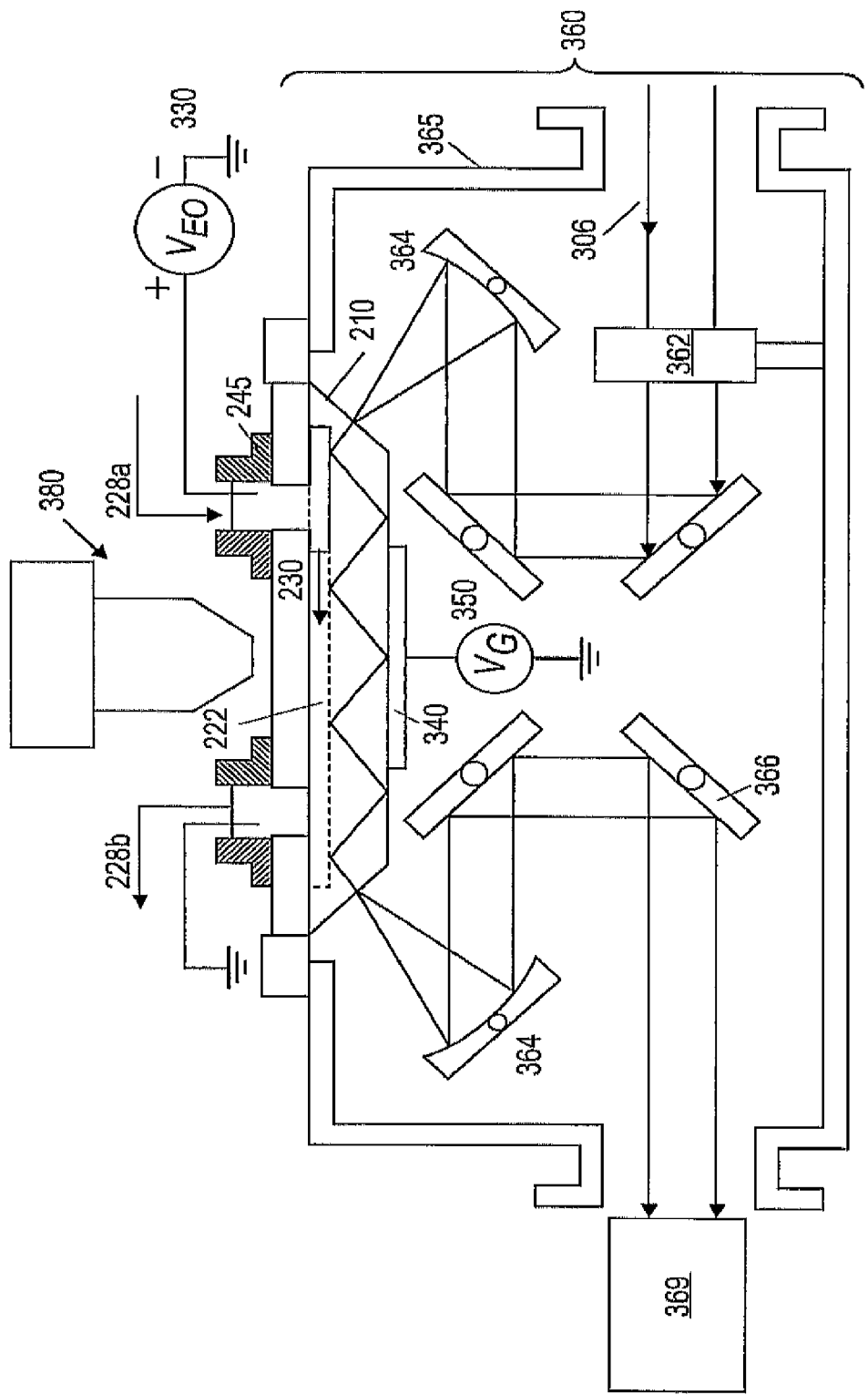
FIG. 3A depicts an exemplary experimental setup including an integrated nanofluidic FET in combination with exemplary analysis systems in accordance with various embodiments of the present teachings.

The buffer solution can be equilibrated for a period of time in order to reach equilibrium of materials, for example, between the buffer solution and the nanochannel walls that include a material of, for example, $SiO_2$. Depending on the system, the equilibrium time can be determined by IR absorbance spectra over time, for example, measured by MIR-FTIRS setup as shown in FIG. 3A. In an exemplary embodiment, after a period of time, if no noticeable changes are detected by IR absorbance spectra, the buffer solution in the nanochannels 222 or the nanoarrays 220 can be assumed to be equilibrated. In embodiments, the equilibrium time can range from about 10 minutes to about 30 minutes, although other equilibrium time can be used depending on the material systems.

In embodiments, the substrate 210 can have beveled edges on both ends that can allow IR access through the substrate and perform multiple internal reflection Fourier transform infrared (MIR-FTIR) spectroscopy to probe molecules in the nanochannels 222, as shown in FIG. 3A. In embodiments, the IR technique used to monitor the system equilibrium can include the IR technique as described in U.S. Pat. No. 7,200,311, entitled "Surface Corrugation on Internal Reflection Infrared Waveguide for Enhanced Detection Sensitivity and Selectivity," which is hereby incorporated by reference in its entirety.

In embodiments, the protein mixture solution can have a protein concentration ranging from a high concentration on the order of millimolar to a low concentration on the order of attomolar. For example, the protein mixture solution can have a protein concentration of about 1 millimolar or less. In embodiments, the protein mixture buffer solution can have low abundance proteins with concentration on the order of picomolar. Such low abundance proteins can be concentrated, focused, separated and/or analyzed by using the nanofluidic devices and systems as described herein.

At 130 of FIG. 1, an electric potential can be applied to a length of the exemplary protein mixture solution in the nanofluidic channels 222 or the nanofluidic arrays 220 to generate a longitudinal electric field along the nanofluidic channels. In embodiments, any suitable power supply as known to one of ordinary skill in the art can be used to apply the electric potential.

In embodiments, suitable electrodes (see 240 in FIG. 2E) can be used to contact the protein mixture solution for the application of electric potential. For example, any conductive material, including any metal-containing material or other known electrodes can be used to contact with the protein mixture solution in the nanofluidic channels 222.

In embodiments, two electrodes (see 240 in FIG. 2E) can be used to apply electric potential through the protein mixture solution and can be spaced apart from each other to form the longitudinal electric field there-between (see FIGS. 2C-2E). In exemplary embodiments, the electrodes can contact the protein mixture solution in the end wells 228 through connectors 245, wherein the center-to-center spacing between the two end wells 228 can range from about 100 μm to about 2 cm or to about 10 cm.

After the electrodes are configured to contact the protein mixture solution that contains one or more proteins, the electric potential can then be applied to generate a longitudinal electric field. The longitudinal electric field can result in one or more focused protein bands 205 as in FIG. 2D.

In an exemplary embodiment, as shown in FIGS. 2C-2E, a negative bias ($V_{EP}$) can be applied to one end well 228, and the opposite side end well 228 can be grounded to induce an electrokinetic flow. In embodiments, the longitudinal electric field (E) along the nanochannels 222 or the arrays 220 can induce an electroosmotic (EO) flow typically with opposing electrophoresis (EP) for negatively charged molecules such as protein molecules that are negatively charged. Because water electrolysis occurs at both electrodes as electric potential is applied, a pH gradient can be established along the longitudinal electric field, which is along the length of the nanochannels 222 or the arrays 220.

In various embodiments, as shown in FIG. 2E, a multi-gate nanofluidic FET control scheme 250 can be used in combination with the focusing/separating system of FIG. 2C. In an exemplary embodiment, a plurality of gates or gate regions 260, for example, formed by highly doped regions of the substrate material such as Si, can be placed along the nanochannels. By locally applying additional electric potentials to the channel walls that encapsulate the protein mixture solution, local pH value and electrical potential in the solution contained in the nanochannels and adjacent to the gate regions 260 can then be dynamically controlled. In this manner, varying electrical potentials, for example, gradient DC potentials, can be applied to the gate regions 260 to dynamically control the pH gradient and electric field gradient in real time along the nanochannels. Further, in embodiments, the multi-gate nanofluidic FET control scheme 250 can allow an application and manipulation of the additional electric potentials to simultaneously control the electrokinetic transport of proteins (e.g., electroosmosis vs. electrophoresis) along the nanofluidic channels.

In embodiments, the multi-gate nanofluidic FET control scheme 250 can include the scheme described in U.S. patent application Ser. No. 11/184,540, entitled "Nanofluidics for Bioseparation and Analysis," which is hereby incorporated by reference in its entirety.

The protein bands 205 can then be focused with each focused band corresponding to at least one protein of the protein mixture solution and therefore to focus and/or separate the proteins. In embodiments, the focused protein band 205 (see FIG. 2D) can be statically focused for a period of time along the longitudinal electric field and then flow forward electrokinetically by electroosmosis/electrophoresis. In embodiments, the focused protein band 205 can be statically focused for a period of time, for example, ranging from about 5 minutes to about 30 minutes. In embodiments, the focused protein band 205 can have a high resolution, i.e., a narrow width of, for example about 100 μm or less, such as about 5 μm.

In embodiments, formation of the protein band 205 and movement of the band 205 through the nanochannels 222 or the nanoarrays 220 can be controlled by controlling the application of the longitudinal electric potential and/or the electric potentials that are applied to individual gates 260 of the multi-gate nanofluidic FETs.

In one embodiment, the location of band formation can be controlled along the longitudinal electric field by increasing or decreasing the electric potential applied to the well 228 as shown in FIG. 2C. For example, as observed in experiments, an increased electric potential can push or advance the proteins move further along the longitudinal electric field and can thus form a focused band even further from its original spot.

In one embodiment, the length of time for forming the focused protein band 205, i.e., from the time when the electric potential is applied to the time when the band forms, can be controlled by controlling the application of electric potential. For example, an increased (or decreased) electric potential can reduce (or increase) the band formation time. This is because the movement of protein bands can be determined by the equilibrium between electrophoresis and electroosmosis, wherein electroosmosis can be much more dominant than other forces such as electrophoresis, ion diffusion, and pH gradient effect in nanochannels having a width of about 100 nm or less. The electric potential modulation can therefore govern the solution flow by electroosmosis in the early stage. That is, an increased (or decreased) electric potential can enhance (or weaken) the electroosmosis flow. In embodiments, as compared with conventional separation techniques, the disclosed systems and methods for focusing/separating proteins can form a focused band in high speed, for example, of about 1 minute or shorter. In a particular example, when focusing protein ovalbumin (OVA) using an electric potential of about −40V, the focused band formation time can be as short as about 10 seconds.

In one embodiment, the movement of proteins in the nanochannels can be controlled, for example, by controlling the amount and/or the direction of the applied electric potential. For example, proteins can be moved repeatably and continuously in both directions along the longitudinal electric field or along the length between the two electrodes through which electric potential can be applied. In an exemplary embodiment, proteins can move in an opposite direction along the longitudinal electric field by increasing or decreasing the electric potential applied. The changed potential can break the electrokinetic equilibrium that is previously formed by the previously applied electric potential. In embodiments, the amount of electric potential can be changed in an alternating fashion, in an increasing fashion or in a decreasing fashion so as to control the flowing directions of the proteins between the two electrodes for repeatable focusing and separation.

In embodiments, the electric potential can be a pre-determined electric potential depending on, for example, molecular weights of proteins in the protein mixture solution. In embodiments, a high molecular weight of proteins may require a high electric potential for the mobility of proteins. In exemplary embodiments, molecular weights of BSA (bovine serum albumin, MW~66,000) and OVA (ovalbumin, MW~45,000) can be 4 times smaller than those of RPE (r-phycoerythrin, MW~240,000) and APC (allophycocyanin, MW~104,000). In embodiments, BSA and OVA can then be highly controllable with a low-magnitude electric potential, for example, as low as −5 $V_{EP}$ due to their low molecular weights. In contrast, RPE and APC bands can appear at a high-magnitude electric potential, for example, with $V_{EP}$>−60 in magnitude.

In embodiments, various proteins can be concentrated, focused, separated and/or analyzed by using the systems and methods as described in FIGS. 1-2. The separation mobility of proteins can be determined by size (i.e., size exclusion) and/or molecular weight of proteins, electrostatic interaction of charged species in the protein mixture solution and electrodes (e.g., the applied electric potential that determines pH gradient generation), etc. Different electric mobilities of proteins can result in protein separation with proteins having different band formation times and band formation locations.

In embodiments, the systems and methods described herein can be used to focus and/or separate proteins for certain protein systems, for example, where proteins having same sign of charge but having sizes slightly different yet in the same size range are mixed in a solution. For example, APC and RPE are large proteins with net negative charges but slightly different in size. In another example, BSA and OVA are small proteins with net negative charges but slightly different in size.

As disclosed, the focused bands of exemplary BSA and OVA in the nanochannels and nanoarrays can be highly selective and very narrow as compared with other methods using microchannels or capillaries. Further, protein focusing and separation as disclosed herein can be achieved by applying a very low electric potential, for example, as low as 3.6 V. Note that, unlike conventional methods, no additional ampholytes nor special buffer ions are used to establish the pH gradient and to induce protein-focusing. Furthermore, the high-resolution protein focusing of BSA and OVA in nanochannels is repeatable.

In this manner, the band formation and separation of proteins can be achieved by isoelectric focusing due to a longitudinal pH gradient along the nanochannels created by water electrolysis occurring on the electrodes 240 in the end wells 228, in conjunction with DFGF due to the force balance of electroosmosis/electrophoresis and ion concentration polarization.

Various embodiments also include an exemplary lab-on-a-chip (LOC) system that serves as an analytical tool and/or as a separation medium for charged molecular species including, but not limited to, proteins, charged dye molecules, or any other charged molecules. The LOC system can include an integrated nanofluidic FET device as disclosed herein in combination with suitable analysis systems. The integrated nanofluidic FET device can include a control scheme of multi-gate nanofluidic field-effect-transistors (FETs), for example, as depicted in FIG. 2E. The LOC system can be used to monitor the flow of an electrolyte solution that contains various charged molecules using, for example, a confocal microscopy. The LOC system can also be used to probe the charged molecules in the electrolyte solution as well as the pH value of the electrolyte solution using, for example, an infrared spectroscopy.

FIG. 3A depicts an exemplary experimental setup including an integrated nanofluidic FET in combination with exemplary analysis systems in accordance with various embodiments of the present teachings. As shown, the setup in FIG. 3A can include a nanofluidic device, for example, the device shown in FIGS. 2A-2E having one or more nanochannel arrays 220. The nanochannel arrays 220 can be covered by an optically transparent material 230. Each nanochannel array 220 can include a plurality of nanochannels 222 (see FIG. 2B) and can be connected with end wells 228a-b (see FIG. 3A) on opposite ends. In embodiments, channel-to-channel dimensional uniformity can be provided in both transverse and longitudinal directions in order to obtain efficient isolation and elution of separated charged molecules.

Figure 3B:
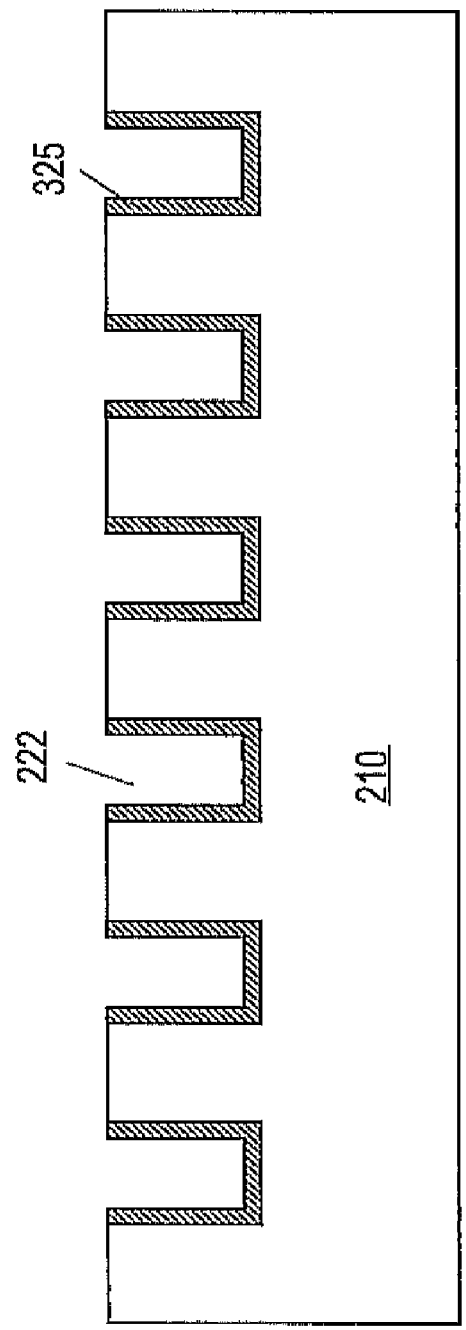
FIG. 3B depicts a cross-sectional view of a portion of an exemplary nanochannel array in accordance with various embodiments of the present teachings.

FIG. 3B depicts a cross-sectional view of a portion of an exemplary nanochannel array 220 with respect to the array shown in FIG. 2B in accordance with various embodiments of the present teachings. As shown, an electrically insulating layer 325, for example, a layer of $SiO_2$, $Si_3N_4$, $Al_2O_3$, $TiO_2$, and/or a combination thereof, can be formed on substrate surfaces of each nanochannel 222, specifically, on the walls and the bottom of each channel. In this case, the electrolyte solution in the nanofluidic channel can be insulated from the substrate 210. In embodiments, the insulating surface layer 325 can have a thickness ranging from about 50 nm to about 500 nm although other thicknesses can also be included for the insulating surface layer 325 in accordance with various embodiments.

In embodiments, the end wells 228a-b can have various cross-sectional shapes including, but not limited to, a circle, a polygon, a star, a rectangle, or a square, wherein the transparent cover 230 can have corresponding holes drilled therethrough in order to facilitate an application of the electrolyte solution into the end wells 228a-b. For example, square-shaped holes can be used for an exemplary Pyrex slip cover and can also be used for the end wells in order to insure an even introduction of the electrolyte solution into each nanochannel 222.

In embodiments, the setup in FIG. 3A can also include a gate contact 340, for example, an FET gate. The FET gate contact 340 can be, for example, a gate metal that makes contact with each of the FET gates or gate regions 260 (see FIG. 2E). In embodiments, the dopants used for the gate regions 260 can include, for example, boron. In an exemplary embodiment, the boron dopant diffusion can be carried out having a dopant level on an order of, for example, about $1 \times 10^{20}$ $cm^{-3}$. The gate regions 260 can have a reduced contact resistance and can be used to efficiently control the surface charge on the insulating surface layer 325 of the nanochannel 222. In embodiments, the gate regions 260 can include a diffusion layer having a diffusion depth ranging from about 0.5 μm to about 5 μm.

In embodiments, the FET gate contact 340 can be configured connecting to each highly doped gate region 260 in the substrate 210, e.g., a silicon substrate. The gate region 260 can be formed in a direction perpendicularly to the channel length and surrounding the nanofluidic channel 222, while the nanochannel array 220 can be fabricated along the direction of IR propagation from an IR source of an IR spectroscopy. In embodiments, the IR spectroscopy can include, for example, multiple internal reflection Fourier transform infrared spectroscopy (MIR-FTIRS) shown by 360 in FIG. 3A.

In embodiments, the substrate 210 with beveled edges can be used as a nanofluidic IR waveguide mounted on a metal housing 365 of the MIR-FTIRS 360 with IR optics including a polarizer 362, and IR mirrors 364, 366. The reflective IR optics can direct the IR beam 306 onto one of the beveled edges of the substrate 210. The IR beam 306 that enters the substrate 210, for example, the Si MIR crystal, can make approximately 35 top reflections from the channel bottom before the beam exits the opposite end of the substrate 210. The IR signal leaving the second beveled substrate edge can be collected by a detector 369, such as a HgCdTe detector. Due to these multiple reflections, the exemplary Si MIR crystal can be opaque to IR, for example, below a wavenumber of about 1500 $cm^{-1}$. In embodiments, the exemplary LOC setup of FIG. 3A can further include, for example, confocal fluorescence microscopy, such as laser-scanning confocal fluorescence microscopy (LS-CFM) shown as 380 in FIG. 3A, configured to monitor the electrolyte solution and the charged species in the nanochannels 222 through the optically transparent cover 230.

In embodiments, the substrate 210 can include a double-side-polished Si(100) wafer in order to prevent the scattering and loss of IR beam intensity during multiple internal reflection in the MIR-FTIRS analysis system 360 as shown in FIG. 3A.

In embodiments, the LOC setup of FIG. 3A can be used, for example, to probe wall-molecule interactions and their impact on ζ-potential; to monitor FET flow control in the nanochannels as well as the pH value of the electrolyte solution in response to a transverse gate electric potential $V_G$; and/or to probe the effect of small, but measurable leakage current through the FET gate during the FET flow control.

For example, the setup of FIG. 3A can be used as an analytical tool using MIR-FTIRS 360 to probe the signature vibrational modes of charged molecules flowing through the nanochannels 222. The spectrum changes in observable vibrational modes can further provide information about diffusion rate, flow speed, and wall adsorption/desorption of molecules, along with a pH shift in the nanochannels.

In embodiments, while maintaining a constant longitudinal electrical field with $V_{EO}$ 330, a DC potential can be applied to each FET gate 260 (see FIG. 2E) through the gate contact 340 to provide the transverse gate bias $V_G$ 350 (also see 250 in FIG. 2E) and to control the surface charge of the insulating layer 325 on channel walls and channel bottoms. That is, the surface charge of the insulating layer 325 and therefore ζ-potential can be modulated by the applied gate potential $V_G$ during the FET flow control. In particular, the modulation of ζ-potential, with concomitant protonation or deprotonation of functional groups of the insulating surface layer 325, for example, functional SiOH groups on $SiO_2$ surfaces, can govern the direction of the electroosmotic (EO) flow generated by the longitudinal electrical field $V_{EO}$ and solution pH in nanochannels.

In embodiments, the flow response to the gate bias during the FET flow control can be virtually immediate and repeatable. In addition, the observed flow response can be independent of the position of charged molecules with respect to the gate position. That is, the flow response can be identical, independent of whether the charged molecules are fore or aft of the gate region.

In embodiments, depending on the sign, polarity, and magnitude of gate bias $V_G$ 350, a pH shift, for example, close to a whole pH unit, can be observed. In embodiments, the pH shift of the electrolyte solution containing charged species can be monitored by a pH indicator including, for example, fluorescein. The molecular structure and therefore the characteristic IR vibrational modes of fluorescein indicator can be strongly dependent on the pH of the buffered electrolyte solution. The solution pH in the nanochannels can therefore be monitored by the IR absorbance result of the pH indicator. Due to the pH shift in the nanochannels, isoelectric focusing of charged molecules including, for example, low-abundance proteins, can be achieved with multiple gates placed along the channels to create a longitudinal pH gradient.

In embodiments, unusual or anomalous flow characteristics, for example, multi-reversed EO flow and pH shift can be obtained, when the FET flow control further contains prolonged application of the gate bias $V_G$ 350. With the prolonged application of the gate bias $V_G$, the initial flow direction and speed and the initial pH response can be reversed and can further be multi-reversed.

In embodiments, the term "prolonged application of gate electric potential $V_G$" refers to a certain amount or a certain level of an application time of the gate electric potential $V_G$, where leakage current through the gate dielectric can cause water electrolysis near the gate region.

In embodiments, the leakage current that flows from the FET gate 260, through the insulating surface layer 325, e.g., the thermally grown $SiO_2$, and to the electrolyte solution in the nanochannels 222 can be measured. Specifically, the leakage current can be measured, for example, from the gate voltage source equipped with a current readout.

Figure 4:
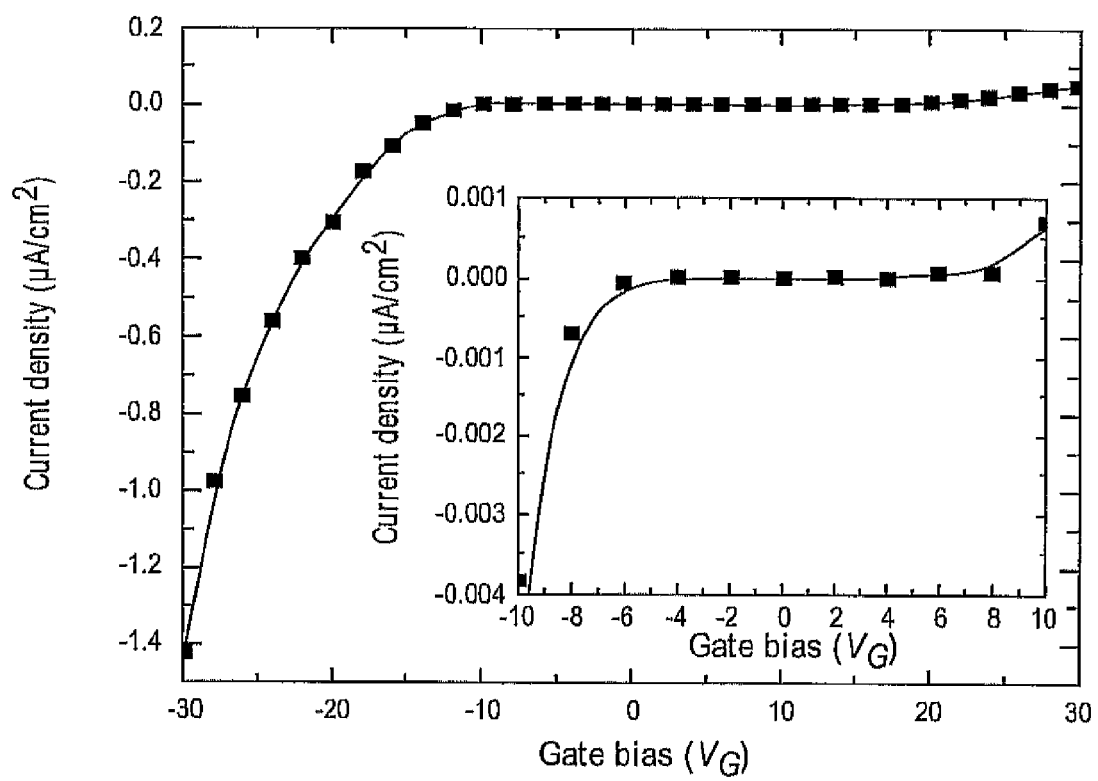
FIG. 4 depicts an exemplary measurement of leakage current density in accordance with various embodiments of the present teachings.

FIG. 4 depicts an exemplary relationship between a leakage current density ($J_{leak}$) and a gate bias $V_G$ that ranges from about −30 V to about +30 V in accordance with various embodiments of the present teachings.

In the illustrated example of FIG. 4, the leakage current density ($J_{leak}$) can be on the order of $nA \cdot cm^{-2}$ for $V_G$ within the range between about −6 V and about +8 V. However, $J_{leak}$ can increase in magnitude up to about −1.4 $\mu A \cdot cm^{-2}$ for $V_G$ below −6 V, and can be up to about 0.05 $\mu A \cdot cm^{-2}$ for $V_G$ above about +10 V. Note the asymmetry in $J_{leak}$, where $J_{leak}$ can be significantly larger in magnitude with a negative gate bias $V_G$ than with a positive gate bias $V_G$. That is, the exemplary $SiO_2$ walls will not be as leaky with a positive gate bias $V_G$ up to about +20 V, whereas a $V_G$ of less than about −10 V can lead to a significant leakage current.

In embodiments, the leakage current can cause water electrolysis in the electrolyte solution to generate $H_3O^+$ or $OH^-$ ions that populate the region near the insulating surface layer 325 surrounded by the gate regions 260 (see FIG. 2E). The generation and accumulation of these $H_3O^+$ or $OH^-$ ions can then reverse the initial flow direction and/or speed, as well as the pH shift set by the gate bias $V_G$.

The following reactions show the water electrolysis and other side reactions that occur at the anode and cathode.

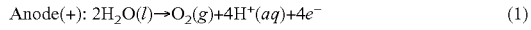
$$\text{Anode}(+): 2H_2O(l) \rightarrow O_2(g) + 4H^+(aq) + 4e^- \quad (1)$$

$$4H^+(aq) + 4H_2O(l) \rightarrow 4H_3O^+(aq) \quad (2)$$

$$H^+(aq) + OH^-(aq) \leftrightarrow H_2O(aq) \quad (3)$$

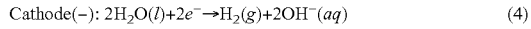
$$\text{Cathode}(-): 2H_2O(l) + 2e^- \rightarrow H_2(g) + 2OH^-(aq) \quad (4)$$

$$O_2(g) + 2H_2O(l) + 4e^- \rightarrow 4OH^-(aq) \quad (5)$$

$$2H^+(aq) + 2e^- \rightarrow H_2(g) \quad (6)$$

In an exemplary embodiment, upon applying a positive gate bias ($V_G > 0V$), the $SiO_2$ surface layer bordering the heavily doped Si gate can serve as an anode, where $O_2$ and $H_3O^+$ ions are generated. The $H^+$ ions produced from the anode can in turn reach equilibrium with $H_2O$. Conversely, when a negative bias $V_G$ is applied to the gate, the $SiO_2$ wall surrounding the gate can serve as a cathode, and $OH^-$ ions can be generated by decomposition of $H_2O$. Note that the side reaction of equation (6) entails that the cathode can deplete $H^+$ ions, that are generated from the anode and have diffused to the cathode, while producing hydrogen gas ($H_2$). This latter reaction can result in a greater absolute magnitude for the rate of increase in pH with a negative gate bias $V_G$ than the absolute magnitude for the rate of decrease in pH with a positive gate bias $V_G$ of equal magnitude.

In exemplary embodiments, the leakage current can flow asymmetrically from the gate defined in the substrate, through the insulating surface layer, to the electrolyte solution and vice versa. In embodiments, the I-V characteristics of the leakage current density can be independent of the buffer used for the electrolyte solution. Examples of the buffers used can include tris-glycine, propionate, and/or NaOH at varying pH values.

In embodiments, in response to FET surface charge (e.g., upon applying $V_G$) and the leakage current (e.g., upon the prolonged application of $V_G$), pH shift can occur in the nanochannels. In embodiments, the pH shift during FET flow control can be monitored using a pH indicator, for example, fluorescein, which can in turn be monitored by an IR spectroscopy. By probing the IR characteristic vibrational modes of fluorescein, such as vibrational peak position and absorbance intensities, pH values of the electrolyte solution can be determined.

For example, IR spectra can show pH-dependent differences due to the protonation/deprotonation of the fluorescein indicator. The neutral fluorescein at low pHs can be a dianion due to the protonation of carboxyl and OH groups of xanthene ring. Thus, fluorescein can be significantly less symmetric. In contrast, fluorescein can have a highly symmetric structure including a xanthene moiety with two identical oxygens by the deprotonation at high pHs.

In embodiments, a calibration curve can be determined or used between the pH value and the IR spectrum result, which shows, for example, intensity ratio of characteristic IR absorbance of the pH indicator. In addition, the calibration curve can be independently verified by, for example, laser absorbance spectroscopy, using SNARF as a pH indicator.

In embodiments, the magnitude of native pH shift in the nanochannel can depend on the initial value of the buffered electrolyte solution and may or may not be a constant shift. In embodiments, the pH shift can be an indirect indicator of the level of electrolysis and therefore the level of $H_3O^+$ or $OH^-$ production caused by electrolysis. In embodiments, a first shift of the pH value of the electrolyte solution can occur upon applying a gate electric potential $V_G$; and a second shift of the pH value of the electrolyte solution can occur upon a prolonged application of the gate electric potential $V_G$ due to water electrolysis caused by the leakage current. In embodiments, the pH shift in nanochannels can be experimentally monitored by the MIR-FTIRS results using a corresponding calibration curve.

For example, the total pH change ($\Delta pH_{total}$) in nanochannels can include two main contributions: (1) the initial protonation/deprotonation of SiOH groups on $SiO_2$ walls upon gate biasing ($\Delta pH_{surf}$), and (2) the generation of $OH^-$ or $H3O^+$ ions by water electrolysis ($\Delta pH_{elect}$) with prolonged gate biasing.

$$\Delta pH_{total} = \Delta pH_{surf} + \Delta pH_{elect}$$

In order to isolate the impact of gate biasing (i.e., $\Delta pH_{surf}$) from that of electrolysis occurring at the two electrodes 240 driving electroosmosis (EO) (i.e., $\Delta pH_{elect}$), the two electrodes 240, e.g., Pt wires, that are inserted into the inlet and outlet wells can be grounded. In an exemplary embodiment, sample IR absorbance spectra can be collected, for example, every 90 seconds, while a DC potential $V_G$ is applied to the gate, for example, varying from about −10V to about 20 V. The observed characteristic peak intensity ratio from IR absorbance can be converted to its corresponding pH value using a corresponding pH calibration curve.

In this example, upon applying a positive gate bias $V_G$ of about +10V, the pH value in nanochannels can be observed to increase, for example, from pH 4.5 to pH 5.3 for about 10 minutes. The positive gate bias can induce positive charges on an exemplary $SiO_2$ walls, by protonation of SiOH groups on channel walls. The positively charged walls can in turn attract negatively charged ions including $OH^-$. The accumulation of $OH^-$ near the walls can then increase the pH value. Thus, the pH increase can qualitatively agree with the accumulation of negative charges and with a reversed flow during FET control.

In embodiments, the initial pH increase can occur over a long period, if the initial positive gate bias is high. For example, when the gate bias is about +30 V, the initial pH increase can occur over a short period of time of about 60 seconds, where double-reversed flow can also be observed.

Following the initial increase in pH, the pH can decrease, e.g., after about 10 minutes with prolonged gate biasing at VG=+10V. This decrease in pH can be due to the production of $H_3O^+$ ions by water electrolysis. In fact, the rate of decrease in pH can be more pronounced as $V_G$ is increased from about +10V to about +20 V. This increase in $V_G$ can cause an increase in leakage current density as shown in FIG. 4. The increased leakage current density can produce $H_3O^+$ ions at a faster rate and subsequently can result in the increased rate of pH decrease.

The pH in the nanochannels can be continuously monitored upon grounding the gate and then switching to a negative gate bias, for example, to about −10 or to about −20 V. For example, $V_G$ can be set to zero for about 10 minutes. Upon grounding the gate region 260 through the gate contact 340, the pH can reach a steady pH value, for example, at about 3.

When a negative gate bias, for example, of about −10 V, is applied, the pH can decrease, e.g., in 3 minutes. This decrease in pH can be caused by the accumulation of positively charged ions, including $H_3O^+$, near the insulating channel walls due to the deprotonation of SiOH groups on $SiO_2$ walls. This pH decrease can qualitatively agree with the accelerated electroosmotic (EO) flow of the electrolyte solution during FET control.

With prolonged negative gate biasing of about −10 V, however, the pH of the buffered electrolyte solution can increase, counteracting the initial decrease, due to the production of $OH^-$ ions from the channel walls by water electrolysis. The rate of increase in pH can be more pronounced as $V_G$ is increased in magnitude from about −10 to about −20 V. The absolute magnitude for this rate of increase can be approximately a factor of two greater than the rate of decrease in pH with a positive gate bias of equal magnitude. This can be because of the depletion of $H^+$ at the negatively biased gate electrode (cathode), in addition to the asymmetrically larger leakage current with a negative gate bias.

In this manner, the observed pH shift in response to the polarity and magnitude of the gate bias can consistently reflect the sign and magnitude of the leakage current.

Figure 5A:
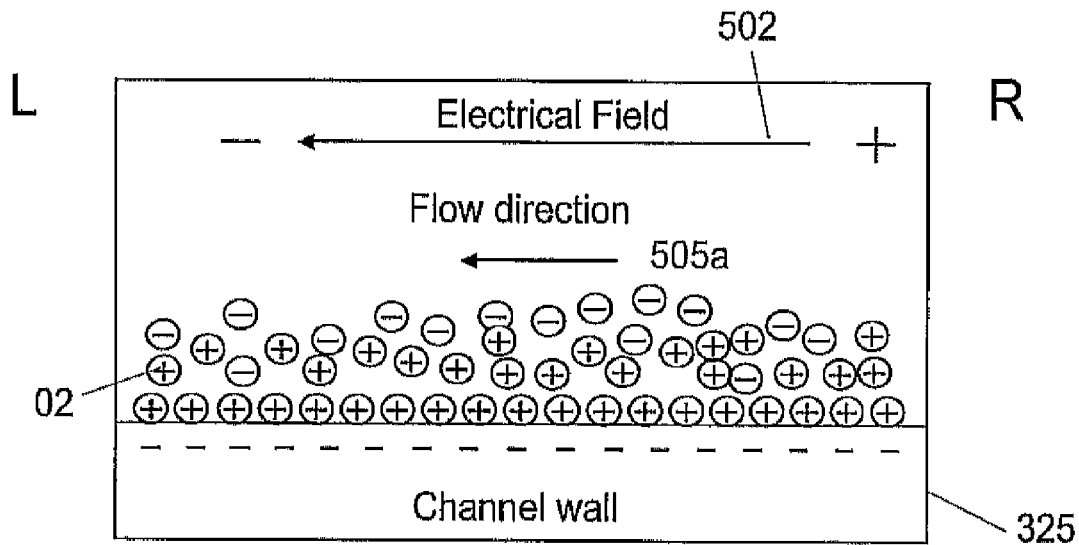
FIGS. 5A-5C depict exemplary models for electroosmotic (EO) flow and pH shift in nanochannels in accordance with various embodiments of the present teachings.
Figure 5B:
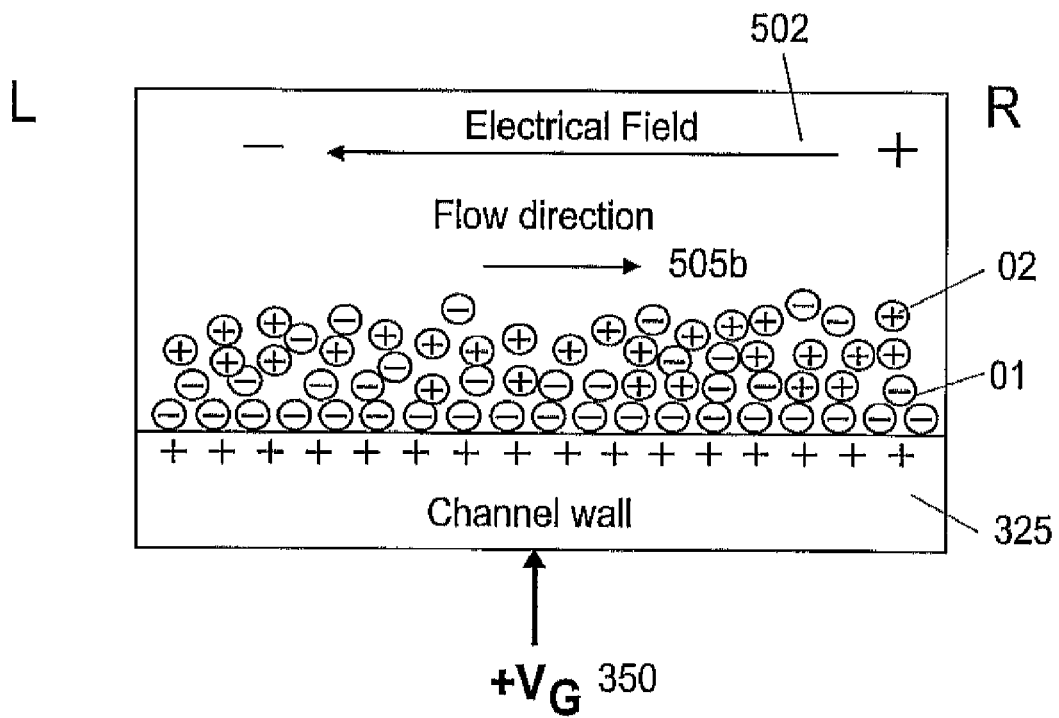
Figure 5C:
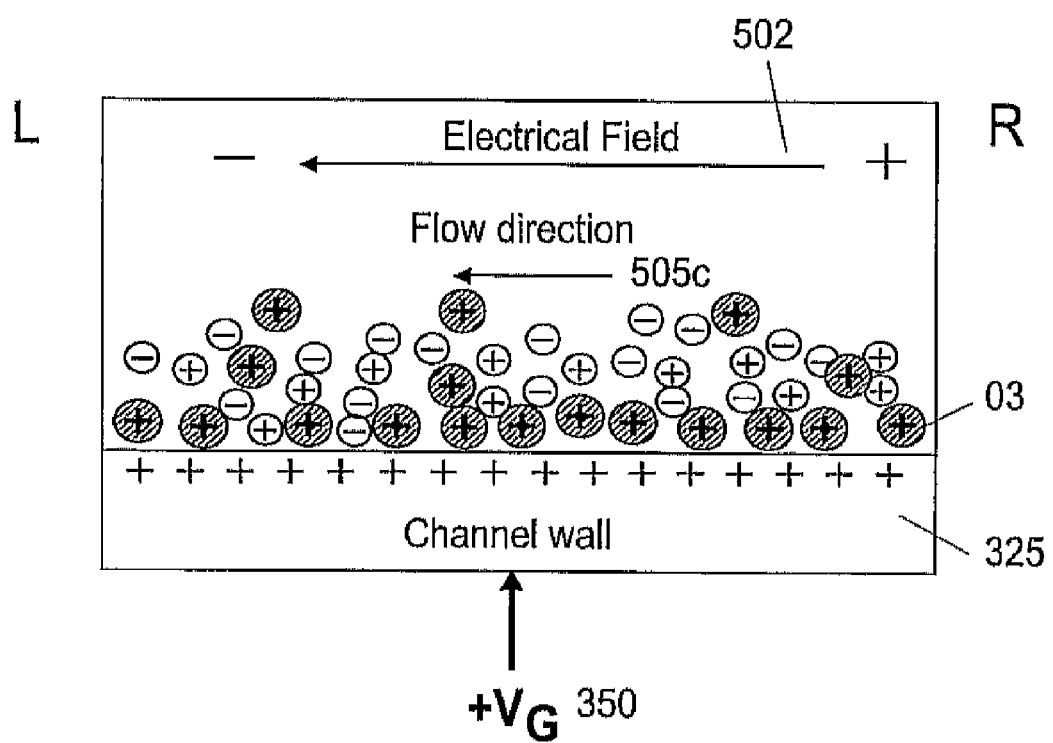

FIGS. 5A-C depict exemplary models showing an EO flow and pH shift over time in nanochannels in accordance with various embodiments of the present teachings. For example, wall adsorption of the charged molecules; electrolysis from leakage current and from the electrodes that drive the electroosmosis; pH shift due to surface charge manipulation and/or from the electrolysis; and diffusion and reaction of $H_3O^+$ and $OH^-$ can be considered in this model. FIGS. 5A-C also schematically describe how the leakage current ultimately induces the double-reversed flow during the FET flow control.

In the exemplary nanofluidic system as shown in FIGS. 5A-C, the initial buffer solution pH can be about 4 and the $SiO_2$ channel walls 325 can be negatively charged. Positively charged counter ions $O_2$ can be accumulated near the channel walls 325.

FIG. 5A shows that upon applying the longitudinal electric field 502 pointing to the left (L) in the illustration, these positively charged ions $O_2$ (e.g., $H_3O^+$ and other positive buffer ions) near the wall 325 can move from right (R) to left, i.e., from anode to cathode, inducing an EO flow 505a.

In FIG. 5B, to reverse the direction of the EO flow 505a, a positive gate bias 350 ($V_G>0V$) can be applied to the gate to raise the $\zeta$-potential. Positively charged ions $O_2$ can be repelled from the walls 325, whereas negatively charged ions 01, e.g., $OH^-$ and other negative buffer ions, can be attracted to the walls 325. Thus, the EO flow can be a reversed EO flow 505b. As shown, this reversal in the direction of EO flow can be induced by the surface charge control.

In FIG. 5C, with a continuing application of the positive gate bias 350 ($V_G>0V$), however, the leakage current through the gate and the $SiO_2$ walls 325 can cause water electrolysis and can generate $H_3O^+$ ions or $H^+$ ions 03 near the surface of the channel walls 325. These positive ions 03 can populate the solution-wall interface by displacing the negative ions 01 that have previously accumulated at the interface. The population of $H_3O^+$ ions or $H^+$ ions 03 can then lead to a double-reversed flow. That is, small, but measurable leakage current through the FET gate during FET flow control can lead to anomalous flow characteristics over time.

A similar phenomenon can occur with a negative gate bias $V_G$ (not shown) that produces $OH^-$ near the gate region, where the EO flow can be accelerated upon the application of the negative $V_G$. The prolonged application of the gate electric potential $V_G$ can then reverse a direction of the EO flow. In this case, multi-reversed flow can also be observed. The difference can include that the accelerated pace of the exemplary double-reversed flow due to the asymmetry in the magnitude of leakage current depending on $V_G$ polarity as indicated in FIG. 4.

In embodiments, the disclosed systems and methods in FIGS. 3-5 can be used for focusing, separating and analyzing proteins with low concentrations, wherein the electrolyte solution can be a protein mixture solution. The focusing and separation of proteins in the protein mixture solution can be controlled and performed by an isoelectric focusing (IEF), a dynamic field gradient focusing (DFGF) and/or a combination thereof using the systems and methods as described in FIGS. 3-5.

EXAMPLES

Example 1

Nanofluidic Device and Characterizations

A nanofluidic separation matrix was fabricated and operated as described in *Lab on a Chip* 2009, entitled "Effect of Wall-Molecule Interactions on Electrokinetic Transport of Charged Molecules in Nanofluidic Channels during FET Flow Control;" in *Lab on a Chip* 2009, entitled "Impact of Leakage Current and Electrolysis on FET Flow Control and pH Changes in Nanofluidic Channels;" and in *Lab on a Chip* 2009, entitled "Experimentally and Theoretically Observed Native pH Shifts in a Nanochannel array;" which are hereby incorporated by reference in their entirety.

An integrated nanofluidic device was fabricated based on semiconductor device fabrication techniques as described in *Lab on a Chip* 2008, entitled "Monitoring FET Flow Control and Wall Adsorption of Charged Fluorescent Dye Molecules in Nanochannels Integrated into a Multiple Internal Reflection Infrared Waveguide," which is hereby incorporated by reference in its entirety.

In this example, the separation platform of the nanofluidic device had seven nanochannel arrays with each array having a width of about 50 μm and a length of about 14 mm formed on a rectangular Si substrate. The substrate had a width of about 1 cm and a length of about 5 cm. Each nanochannel array of the device included approximately a hundred twenty parallel nanochannels. The dimensions of each nanochannel were about 100 nm width×400 nm depth×14 mm length. Nanochannels were fabricated using interferometric lithography (IL) and plasma etching of Si. A thermally grown $SiO_2$ layer (~100 nm) was used as an electrically insulating layer between Si nanochannel walls and the fluid. The nanochannels were sealed with a Pyrex cover by anodic bonding to form the nanofluidic device.

Optical transparency through the anodically bonded Pyrex cover allowed access to laser-scanning confocal fluorescence microscopy [LS-CFM, Zeiss Axioskop (Chester, Va.) with an LSM5 scanning head] from the top, while IR-transparency through the Si substrate with beveled edges allowed access to multiple-internal reflection Fourier transform infrared spectroscopy (MIR-FTIRS, Nicolet 870 with a mid-IR HgCdTe detector).

Example 2

System Equilibrium

The solution reservoirs (i.e., end wells) and nanochannels were first filled completely with a buffer solution by capillary force. Approximately 30 minutes lapsed before the system reached equilibrium between the buffer solution and $SiO_2$ channel walls. This was based on an observation that no noticeable changes were detected in IR absorbance spectra after 30 minutes. A mixture of proteins was then introduced to one of the wells (as an inlet), and a platinum wire was inserted into each well as an electrode. An electric potential (V) was applied to the protein-containing well, while grounding the other well to create a longitudinal electric field (E) along the nanochannels and to induce an electroosmotic (EO) flow typically with opposing electrophoresis (EP) for negatively charged molecules and to create a longitudinal pH gradient by electrolysis occurring at the electrodes.

Example 3

Buffers and Proteins

Sodium phosphate buffer was used in the exemplary experiments with a buffer pH of 7.2 and an ionic strength of 10 mM. All proteins were diluted to ~0.02 μg/mL in the buffer solution in experiments.

Various exemplary proteins were used as examples. Allophycocyanin (APC), r-phycoerythrin (RPE), bovine serum albumin (BSA) conjugated with Alexa Fluor® 488, and ovalbumin (OVA) conjugated with Alexa Fluor® 555 (see Table 1), were purchased from Invitrogen Corporation (Carlsbad, Calif.) and were used as examples for analyzing proteins using the disclosed systems and methods. Green fluorescent proteins (GFPs) were purchased from Upstate Biotechnology (Lake Placid, N.Y.) and were used to represent small proteins with net positive charge. Molecular weights, isoelectric points, net charges, and specifications on fluorescence (i.e., absorbance, emission, and excitation) of the exemplary proteins are summarized in Table 1.

TABLE 1

|  | R-phycoerythrin | Allophycocyanin | GFP | Bovine Serum Albumin -Alexa Fluor 488 | Ovalbumin -Alexa Fluor 665 |
|---|---|---|---|---|---|
| Isoelectric point | 5.1~4.2 | 4.8~4.95 | 5.67 | 4.47~4.85 | 4.43 |
| Molecular weight | 240,000 | 104,000 | 30,000 | 66,000 | 45,000 |
| Abs (nm) | 480, 546, 565 | 650 | 515 |  |  |
| EM (nm) | 578 | 660 | 509 | 519 | 519 |
| EX (nm) | 568-590 | 633 | 488 | 488 | 555 |
| Net charge | Negative | Negative | Positive | Negative | Negative |

Example 4

Protein Focusing of BSA and OVA

Protein focusing was conducted with an exemplary mixture of BSA ($I_P$=4.47~4.85) and OVA ($I_P$=4.43). BSA and OVA are small proteins with sizes slightly different and are all with net negative charges.

In this example, a time series of schematic images from the BSA/OVA mixture was observed by LS-CFM in one of the seven nanochannel arrays. The BSA/OVA mixture can include protein BSA-Alexa Fluor® 488 conjugates with $EM_{BSA}$=488 and protein OVA-Alexa Fluor® 555 conjugates with $EM_{OVA}$=567. A negative potential, $V_{EP}$=−5, was applied to the inlet well (a right well as shown in FIGS. 2C-2E) in which proteins were introduced.

As observed, for about 36 minutes after the electric potential was applied, proteins were not detected in the nanochannels. This is because electroosmosis flow from left to right was strongly dominant than electrophoresis in nanochannels. In the 37$^{th}$ minute, however, OVA was appeared and focused near the inlet well forming a very sharp band of ~5 μm in width.

As also observed, BSA repeatably advanced ahead of OVA from the inlet well in all experiments. The high-resolution focusing of these two proteins continued for about 15 minutes. Then, two bands flowed at 1 μm/s by electrophoresis and became dispersed after traversing 2 mm from the inlet well. Proteins may pass through their isoelectric point due to electrophoresis.

Example 5

Repeatable High-Resolution Protein Focusing of BSA and OVA

The high-resolution protein focusing of BSA and OVA in nanochannels was repeatable. The high-resolution focusing of these two proteins was monitored and demonstrated once again by increasing the electric potential ($V_{EP}$). A time-series snap shots of electrokinetic flow and high-resolution focusing of BSA and OVA were also observed when the electric potential ($V_{EP}$) magnitude was increased from −5 to −10 V. The time-series snap shots were taken every 2 minutes. Note that a portion of proteins was randomly dispersed in nanochannels since they previously flowed from right to left by electrophoresis (see Example 4). Upon applying −10 $V_{EP}$, BSA and OVA quickly flowed back towards the inlet well at 7.3 µm/s for 6 minutes. This flow was induced because the increased electric potential breaks electrokinetic equilibrium and makes the electroosmosis flow from left to right more dominant than electrophoresis.

In this Example 5, the focused band position was 300 µm from the inlet well, which is farther than the distance observed from the lower electric potential ($V_{EP}$=−5) in Example 4. This indicates that the isoelectric points of proteins moved farther into the nanochannels as the pH gradient changed due to the higher magnitude of electric potential (−10 $V_{EP}$). After stationary focusing of the two proteins for about 12 minutes, they flowed farther into the nanochannels at 0.3 µm/s for 12 minutes.

Upon continuous biasing, the two proteins started to flow again from right to left and became dispersed after flowing approximately 3 mm from the inlet well. This result was consistent with the results shown in Example 4. However, a sharp band of OVA and a portion of BSA were observed remaining in the nanochannels. While not desiring to be bound by any particular theory, this may have been caused by: (1) adsorption of proteins to the nanochannel walls or (2) continuous protein focusing after most of the proteins have moved out of their isoelectric point by electrophoresis.

Example 6

Protein Separations

To achieve clear band separation of proteins, a protein mixture including BSA, OVA, RPE, APC, and GFP were used in various combinations. As a result, in the range of electric potential from −5 to −40 $V_{EP}$, BSA and OVA always appeared and formed sharp bands. In contrast, RPE, APC, and GFP did not form bands until the electric potential was raised to −40 $V_{EP}$. However, upon applying −60 $V_{EP}$, RPE and APC both appeared forming sharp bands near the inlet well, while GFP still did not appear in the nanochannels.

GFP (MW ~30,000) was not shown in the range of electric field ($V_{EP}$=−5-60) as studied here, although the molecular size was the smallest. This phenomenon is likely due to the electrostatic charge interaction of charged GFP and the cathode. Therefore, the pH value in the nanochannel was estimated to be approximately 6 at which GFP was positively charged, while positively charged GFP did not flow into the nanochannels as long as the negative potential was applied to the inlet electrode (the cathode).

In experiments, BSA was observed to have a higher mobility than OVA, and this mobility difference was used for separation. Various experiments also included focusing and separation of BSA and OVA by modulating the magnitude of the electric potential ($V_{EP}$) from −20 to −40 V.

As observed in the particular experiment, band formations of BSA and OVA were achieved in 5 minutes upon applying an electric potential of about −40 $V_{EP}$. This band formation occurred more quickly than in the case of using a low electric potential ($V_{EP}$). These band formations continued for 8 minutes. When the electric potential magnitude was lowered to −20 $V_{EP}$, these bands quickly moved from right to left (e.g., from the $10^{th}$ minute to the $18^{th}$ minute) at 60 µm/s. That is, the low-magnitude (−20V) weakened the electroosmosis flow, inducing bands of proteins to move from right to left. The protein bands again moved back towards the inlet upon raising the electric potential magnitude to −40 $V_{EP}$, and again its direction reversed upon lowering the magnitude to −20 $V_{EP}$. This observation was highly repeatable. The other significant phenomenon observed meanwhile was a separation of BSA and OVA. Upon lowering the electric potential magnitude to −20 $V_{EP}$, BSA completely moved back to the inlet, whereas OVA was still focused and remained at the same position.

Example 7

Nanofluidic Lab-on-a-Chip System

Double-side-polished Si (100) wafers about 1 cm wide and about 5 cm long were used as the substrate. A 3-mm wide boron doped gate region was defined perpendicularly to the channel direction at the center of the wafer. The dopant diffusion was carried out for about 60 minutes at about 1050° C. in an $O_2/N_2$ environment, which resulted in the formation of a diffusion layer with a depth of about 1-1.2 µm and a dopant level on the order of about $1 \times 10^{20}$ $cm^{-3}$. An array of nanochannels was fabricated along the direction of IR propagation, using interferometric lithography (IL) and plasma etching.

Immediately after the etching, each channel was approximately 200 nm wide and 450 nm deep. The nanochannel array occupied a total area of about 3 mm wide by 16 mm long, which contained up to about 8000 nanochannels. A thermal $SiO_2$ layer was grown up to about 100 nm, reducing the channel width to about 100 nm and the channel depth to about 400 nm.

Example 8 pH Shift in Nanochannels

A buffer solution was introduced into the nanochannels by capillary force. Platinum (Pt) wires were used as electrodes immersed in two solution wells on opposite ends of the channels. To induce an electroosmotic flow along the channels, a positive potential ($V_{EO}$>0) was applied to the inlet, and the outlet was grounded, generating a longitudinal electrical field.

After the electroosmotic flow was induced, a potential ($V_G$) was applied to the highly doped gate to modulate the surface charge on channel walls and to conduct FET flow control. $V_{EO}$ and $V_G$ shared a common ground to maintain the same reference potential.

During the FET control, the flow of fluorescent dye molecules in the nanochannels was monitored by LS-CFM. Alexa 488 maleimide was used as an example to visualize the FET flow control with LS-CFM, because the fluorescence intensity of Alexa 488 was strong and stable in a relatively wide pH range from about 4 to about 9. The excitation and emission wavelengths of Alexa 488 were about 488 nm and 519 nm, respectively.

In the FET flow control experiments, Alexa 488 was dissolved in a pH 4 buffer, since $SiO_2$ channel walls have an isoelectric point (pKa) of about 3.7, where the net charge on the surface is zero. Above the isoelectric point, the surface charge became increasingly negative, as surface hydroxyl groups (SiOH) became deprotonated. Conversely, the surface charge gradually turned off or became further protonated as $[SiOH_2]^+$, as pH decreased below pKa. Therefore, the surface charge control and its impact on FET flow control were relatively more pronounced near the isoelectric point.

To monitor the pH shift, a buffer solution was injected with a desired pH value ranging from about 2 to about 8 into the nanochannels, and the system was allowed to equilibrate for approximately 20 minutes, after which no noticeable change in IR spectrum was observed. An IR background spectrum was taken with 2 cm$^{-1}$ resolution averaged over 100 scans. Taking the background only with the buffer solution minimized interference from absorption bands of water, when sample spectra were taken with fluorescein solution. The channels were then cleaned in DI water and dried on a hot plate. A buffer solution of fluorescein ($C_{20}H_{12}O_5$) dye molecules with a known pH was then injected into one of the two solution wells to fill the nanochannels, and a series of sample IR spectra with the same resolution and averaging were taken to monitor the characteristic vibrational modes of fluorescein dye molecules that are sensitive to the pH shift.

Fluorescein was a commonly used fluorescent dye molecule, whose quantum yield was strongly affected by solution pH. The absorption and emission wavelengths of fluorescein are about 494 and 521 nm, respectively. The variation in quantum yield for fluorescein was monitored with FTIR spectroscopy to relate a pH shift to the molecule's structural change. Depending on the pH of buffer solutions, fluorescein can become a cation (pKa <2.08), a neutral molecule (pKa=2.08~4.31), an anion (pKa=4.31~6.43) or a dianion (pKa >2.08) by protonation or deprotonation of carboxyl group and OH group on the molecule. Thus, the pH in nanochannels was monitored by analyzing the molecular structure of charged species using MIR-FTIRS.

Deuterated water ($D_2O$, 99.9 atom % D, obtained from Sigma-Aldrich) instead of $H_2O$ was used to avoid overlapping between the vibrational modes of $H_2O$ [vs(OH) at 3400~3000 cm$^{-1}$ and $\delta$s(HOH) at 1640 cm$^{-1}$], and those of fluorescein [vs($CH_x$) and vas($CH_x$) at 3000-2800 cm$^{-1}$ and vas($COO^-$) and vs(C—C) at 1600-1580 cm$^{-1}$].

Various buffers were used to monitor IR spectra of fluorescein in different pH buffer solutions from pH 2 to 8. Chloroacetic acid (pKa=2.83) buffer was used for pH 2 to 3, acetate buffer (pKa=4.76) was used for pH 4-5, pyridine buffer (pKa=5.23) was used for pH 6, phosphate buffer (pKa=7.2) was used for pH 7, and tris-glycine buffer (pKa=8.02) was used for pH 8. The pH for each buffer was adjusted with HCl or NaOH, and the ionic strength of all buffer solutions was approximately adjusted to about 1-2 mM. At this ionic strength, $\lambda_D$ (1/k) is approximately about 10 nm determined by unit charge, dielectric permittivity, vacuum dielectric constant, Boltzmann's constant, temperature, valence charge, and charge density.

Example 9

Reversed EO Flow in Nanochannels

Using LS-CFM, the FET flow control was monitored with Alexa 488 maleimide (1 mg·mL$^{-1}$) dissolved in a pH 4 buffer solution. After filling the nanochannels only with the buffer solution, Alexa 488 was injected into the inlet well. To induce an EO flow in the nanochannels, a $V_{EO}$ of about +6 V was applied to the right-side well in FIG. 3A, where Alexa 488 was contained, while the opposite well on the left side was grounded. The electroosmotic flow of Alexa 488 moving from the right side ($V_{EO}$=+6) to the left side (grounded) was at a rate of about 3.2 μm·s$^{-1}$.

With a constant longitudinal electrical field with $V_{EO}$, when a negative bias ($V_G$=−30V) was applied to the gate to lower the ζ-potential, the flow velocity of Alexa 488 was increased to about 25 μm·s$^{-1}$ moving from right to left at an accelerated pace. The enhanced flow velocity upon applying the negative $V_G$ was an order of magnitude greater than the EO flow velocity of about 3.2 μm·s$^{-1}$, which was induced by the longitudinal electrical field but without $V_G$. Conversely, Alexa 488 rapidly reversed its flow when the $V_G$ of +30V was applied to the gate to raise the ζ-potential.

Confocal images of Alexa 488 upon inducing an EO flow with $V_{EO}$ of about +6V and subsequently applying a positive gate bias $V_G$ (+30V) shows that after inducing the reverse flow with the positive $V_G$, the speed and direction of EO flow are not maintained constantly over time. When the EO flow was moving from right to left at 3.2 μm·s$^{-1}$, upon applying the positive gate bias ($V_G$=+30V), Alexa 488 reversed its flow moving from left to right for about 60 seconds and then started to reverse its flow again moving to the left.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. The term "at least one of" is used to mean one or more of the listed items can be selected.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume values as defined earlier plus negative values, e.g. −1, −1.2, −1.89, −2, −2.5, −3, −10, −20, −30, etc.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for controlling an electrolyte solution in a nanofluidic channel comprising:
   providing a plurality of nanofluidic channels in a substrate, wherein each nanofluidic channel comprises an insulating surface layer such that an electrolyte solution in the nanofluidic channel is insulated from the substrate;
   configuring a multi-gate nanofluidic field-effect-transistor (FET) having a plurality of FET gates formed in the substrate, wherein the plurality of FET gates are spaced along a length direction of each nanofluidic channel with each FET gate surrounding the nanofluidic channel;

applying an electric potential $V_{EO}$ to a length of the electrolyte solution in each nanofluidic channel to generate an electroosmotic (EO) flow of the electrolyte solution along the nanofluidic channel; wherein the electrolyte solution comprises a plurality of charged species; and applying a gate electric potential $V_G$ to each FET gate to generate a leakage current to change at least one of a direction of the EO flow and a speed of the EO flow.

2. The method of claim 1, wherein the leakage current flows from each FET gate, through the insulating surface layer of the nanofluidic channel, and to the electrolyte solution in the nanofluidic channel.

3. The method of claim 1, wherein the insulating surface layer comprises $SiO_2$ and wherein a leakage current density is larger in magnitude with a negative gate electric potential $V_G$ than with a positive gate electric potential $V_G$.

4. The method of claim 1 further comprising:
applying a gate electric potential $V_G$ to accelerate the EO flow; and
continuing the application of the gate electric potential $V_G$ to reverse a direction of the EO flow caused by the leakage current.

5. The method of claim 1 further comprising:
applying a gate electric potential $V_G$ to reverse the direction of the EO flow; and
continuing the application of the gate electric potential $V_G$ to generate a double-reversed EO flow caused by the leakage current.

6. The method of claim 1, wherein the direction and the speed of the EO flow are maintained inconstantly over time after an initial reverse of EO flow upon applying the gate electric potential $V_G$.

7. The method of claim 1, wherein the change of the direction and the speed of the EO flow is independent of the position of the charged species with respect to the position of the FET gate.

8. The method of claim 1, further comprising:
a first change of the pH value of the electrolyte solution upon applying the gate electric potential $V_G$; and
a second change of the pH value of the electrolyte solution by a prolonged application of the gate electric potential $V_G$ due to water electrolysis caused by the leakage current.

9. The method of claim 1, further comprising:
increasing the pH value of the electrolyte solution upon applying a positive gate electric potential $V_G$;
decreasing the pH value of the electrolyte solution by a prolonged application of the positive gate electric potential VG due to water electrolysis caused by the leakage current;
decreasing the pH value of the electrolyte solution upon applying a negative gate electric potential $V_G$; and
increasing the pH value of the electrolyte solution by a prolonged application of the positive gate electric potential VG due to water electrolysis caused by the leakage current.

10. The method of claim 1, wherein the pH of electrolyte solution ranges from about 4 to about 9 and shifts by a pH unit upon applying the gate electric potential $V_G$.

11. The method of claim 1 further comprising measuring the pH value of the electrolyte solution using a calibration curve, wherein the calibration curve renders a relationship between an IR result of the charged species and the pH value of the electrolyte solution.

12. The method of claim 1 further comprising using a pH indicator to monitor the pH change of the electrolyte solution, wherein the pH indicator comprises a fluorescein monitored by IR absorbance.

13. The method of claim 1 further comprising isoelectrically focusing the plurality of charged species in the electrolyte solution in the nanofluidic channels by a controlled pH shift, wherein the charged species comprises proteins.

14. The method of claim 1, further comprising applying the gate electric potential $V_G$ to each FET gate to generate the leakage current to further change a pH value of the electrolyte solution.

15. A method for controlling an electrolyte solution in a nanofluidic channel comprising:
providing a plurality of nanofluidic channels in a substrate, wherein each nanofluidic channel comprises an insulating surface layer such that an electrolyte solution in the nanofluidic channel is insulated from the substrate;
configuring a multi-gate nanofluidic field-effect-transistor (FET) having a plurality of FET gates formed in the substrate, wherein the plurality of FET gates are spaced along a length direction of each nanofluidic channel with each FET gate surrounding the nanofluidic channel;
applying an electric potential $V_{EO}$ to a length of the electrolyte solution in each nanofluidic channel to generate an electroosmotic (EO) flow of the electrolyte solution along the nanofluidic channel; wherein the electrolyte solution comprises a plurality of charged species; and
applying a gate electric potential VG to each FET gate to generate a leakage current to change at least one of a direction of the EO flow and a speed of the EO flow; wherein the leakage current flows from each FET gate, through the insulating surface layer of the nanofluidic channel, and to the electrolyte solution in the nanofluidic channel.

16. The method of claim 15 further comprising:
applying a gate electric potential $V_G$ to accelerate the EO flow or to reverse the direction of the EO flow; and
continuing the application of the gate electric potential $V_G$ to further reverse the direction of the EO flow caused by the leakage current.

17. The method of claim 15, further comprising:
a first change of the pH value of the electrolyte solution upon applying the gate electric potential $V_G$; and
a second change of the pH value of the electrolyte solution by a prolonged application of the gate electric potential $V_G$ due to water electrolysis caused by the leakage current.

18. The method of claim 15 further comprising probing the charged species flowing in the nanofluidic channels using IR spectroscopy, wherein the IR spectroscopy comprises multiple internal reflection Fourier transform infrared spectroscopy (MIR-FTIRS).

19. The method of claim 15, further comprising applying the gate electric potential VG to each FET gate to generate the leakage current to further change a pH value of the electrolyte solution.

\* \* \* \* \*